US012737046B2

(12) United States Patent
Antonakis

(10) Patent No.: US 12,737,046 B2
(45) Date of Patent: Sep. 15, 2026

(54) WRITING INSTRUMENT

(71) Applicant: BIC Violex Single Member S.A., Anoixi (GR)

(72) Inventor: Ion-Ioannis Antonakis, Anoixi (GR)

(73) Assignee: BIC Violex Single Member S.A., Anoixi (GR)

( * ) Notice: Subject to any disclaimer, the term of this patent is extended or adjusted under 35 U.S.C. 154(b) by 553 days.

(21) Appl. No.: 18/314,975

(22) Filed: May 10, 2023

(65) Prior Publication Data

US 2023/0364936 A1 Nov. 16, 2023

(30) Foreign Application Priority Data

May 12, 2022 (EP) .................................... 22173001

(51) Int. Cl.
*B43K 29/18* (2006.01)
*A61B 5/00* (2006.01)
(Continued)

(52) U.S. Cl.
CPC .............. *G06F 3/016* (2013.01); *A61B 5/681* (2013.01); *B43K 29/18* (2013.01); *G06F 3/03545* (2013.01); *G06F 3/041* (2013.01); *G06F 9/453* (2018.02); *G10L 17/02* (2013.01); *H04B 11/00* (2013.01); *H04L 51/02* (2013.01); *A61B 5/02405* (2013.01); *A61B 2560/0468* (2013.01)

(58) Field of Classification Search
CPC ...... G06F 3/016; G06F 3/03545; G06F 3/041; G06F 3/015; G06F 3/167; G06F 9/453;
(Continued)

(56) References Cited

U.S. PATENT DOCUMENTS 4,581,491 A 4/1986 Boothroyd
9,579,060 B1 * 2/2017 Lisy ....................... A61B 5/165
(Continued)

FOREIGN PATENT DOCUMENTS

EP 0167471 A2 1/1986
KR 20090012145 U 12/2009
(Continued)

OTHER PUBLICATIONS

A. Siennicka, D.S. Quintana, P. Fedurek, A. Wijata, B. Paleczny, B. Ponikowska, D.P. Danel, Resting heart rate variability, attention and attention maintenance in young adults, International Journal of Psychophysiology, vol. 143, 2019, pp. 126-131, ISSN 0167-8760, https://doi.org/10.1016/j.ijpsycho.2019.06.017. (https://www.sciencedirect.com/science/article/pii/S0167876019301898).
(Continued)

*Primary Examiner* — Christopher E Leiby
(74) *Attorney, Agent, or Firm* — Bookoff McAndrews, PLLC

(57) ABSTRACT

A computer-implemented method for audio to tactile enhancement comprising obtaining audio data comprising a sample of speech, generating at least one haptic cue definition by performing a first signal processing operation on at least one portion of the audio data, and actuating a haptic actuator comprised in a user device or a writing instrument according to the at least one haptic cue definition. Examples concern obtaining a pulse signal representing a pulse of a user of the user device or the writing instrument, wherein the pulse signal is obtained substantially simultaneously with obtaining the audio data and applying a second signal processing operation to the pulse signal, wherein the second signal processing operation calculates a heart rate variability signal of the user.

18 Claims, 9 Drawing Sheets

(51) Int. Cl.

| | |
|---|---|
| ***G06F 3/01*** | (2006.01) |
| ***G06F 3/0354*** | (2013.01) |
| ***G06F 3/041*** | (2006.01) |
| ***G06F 9/451*** | (2018.01) |
| ***G10L 17/02*** | (2013.01) |
| ***H04B 11/00*** | (2006.01) |
| ***H04L 51/02*** | (2022.01) |
| *A61B 5/024* | (2006.01) . |

(58) Field of Classification Search

CPC ..... A61B 5/681; A61B 5/02405; A61B 5/746; A61B 5/02433; A61B 5/6898; A61B 5/7275; A61B 5/02444; A61B 5/168; A61B 5/7455; A61B 2560/0468; B43K 29/18; B43K 29/08; G10L 17/02; G10L 25/90; G10L 21/16; H04B 11/00; H04L 51/02; A61F 11/04

See application file for complete search history.

(56) References Cited

U.S. PATENT DOCUMENTS

| | | | | |
|---|---|---|---|---|
| 2010/0191135 | A1 | 7/2010 | Kuo et al. | |
| 2011/0102160 | A1 | 5/2011 | Heubel et al. | |
| 2017/0115755 | A1* | 4/2017 | Jung | G06F 3/0383 |
| 2018/0067558 | A1* | 3/2018 | Eagleman | G09B 21/04 |
| 2018/0325738 | A1 | 11/2018 | Aghamohammadi | |
| 2024/0033466 | A1* | 2/2024 | Nazarian | A61H 9/0078 |
| 2025/0040883 | A1* | 2/2025 | Westerink | A61B 5/7275 |
| 2025/0054623 | A1* | 2/2025 | Yellowlees | G06F 40/58 |

FOREIGN PATENT DOCUMENTS

| | | | |
|---|---|---|---|
| WO | 2008150909 | A1 | 12/2008 |
| WO | 2009155458 | A1 | 12/2009 |
| WO | 2017105976 | A1 | 6/2017 |
| WO | 2017106044 | A1 | 6/2017 |

OTHER PUBLICATIONS

Aimie-Salleh, Noor & Ghani, Nurul & Hasanudin, Nurhafiezah & Shafie, Siti. (2019). Heart Rate Variability Recording System Using Photoplethysmography Sensor. 10.5772/intechopen.89901.

European Search Report issued in European Application No. 22173001.3, mailed on Nov. 24, 2022.

Task Force of the European Society of Cardiology the North American Society of Pacing Electrophysiology, “Heart Rate Variability—standards of measurement, physiological interpretation, and the clinical use”, journal Circulation, vol. 93, No. 5, pp. 1043-1065, 1996, {10.1161/01.CIR.93.5.1043}, https://www.ahajournals.org/doi/abs/10.1161/01.CIR.93.5.1043.

* cited by examiner

WRITING INSTRUMENT

This application claims priority from European patent application No. 22173001.3, filed on May 12, 2022, the contents of which are hereby incorporated herein in their entirety by this reference.

TECHNICAL FIELD

The embodiments described herein concern a computer-implemented method for audio to tactile enhancement, and an associated writing instrument, system, computer program element, and computer readable medium.

BACKGROUND

For many people, the fidelity of aural comprehension of speech given by presenter or teacher in a lecture theatre, classroom, or another type of presentation room is affected by a range of factors. A listener may be separated by a long distance from the presenter, causing a large attenuation of the magnitude of the original sound from the presenter. Disruptive individuals in the lecture theatre or classroom can sometimes generate noise affecting the aural comprehension of speech from a presenter. Poor room acoustics can also degrade the quality of sound reaching a listener.

Physical obstacles in a room (such as a pillar located between a presenter and a listener) can present a problem for those with hearing imperfections, because such individuals are often reliant on being able to watch the movement of a presenter's lips in order to enhance the perception of some words.

Public address systems can be installed in classrooms or lecture theatres to increase the volume of speech from a presenter or teacher. Often, however, such systems are incorrectly configured, so that feedback, signal interruption caused by loose wires, radio frequency interference of radio microphones from mobile telephones, incorrectly positioned loudspeakers, and poor operator training in the use of public address systems compounds the problem of aural comprehension rather than enhancing aural perception as intended.

Accordingly, further measures can be taken to facilitate a listener's aural comprehension of speech from a presenter in a lecture theatre, or classroom.

SUMMARY

According to a first aspect, there is provided a computer-implemented method for audio to tactile enhancement comprising:

- obtaining audio data comprising a sample of speech;
- generating at least one haptic cue definition by performing a first signal processing operation on at least one portion of the audio data; and
- actuating a haptic actuator comprised in a user device or a writing instrument according to the at least one haptic cue definition.

According to a second aspect, there is provided a writing instrument for audio to tactile enhancement, comprising a processor and a haptic actuator.

The processor is configured to obtain audio data comprising a sample of speech, to generate at least one haptic cue definition by performing a first signal processing operation on at least one portion of audio data, and to actuate the haptic actuator according to the at least one haptic cue definition.

According to a third aspect, there is provided a system, comprising a writing instrument according to the second aspect or its examples, and a user device comprising a pulse sensor and a wireless communication interface. The user device is configured to measure a pulse signal of a user of the user device using the pulse sensor, and to compute a heart rate variability signal of the user based on the pulse signal, and wherein the user device is configured to transmit the heart rate variability signal of the user to the writing instrument via a wireless communication interface of the user device.

According to a fourth aspect, there is provided a computer program element comprising machine readable instructions which, when executed by a processor, are configured to cause the processor to perform the computer-implemented method according to the first aspect, or its embodiments.

According to a fifth aspect, there is provided a computer readable medium comprising the computer program element according to the fourth aspect.

An effect is that by transforming speech signals of a spoken presentation into tactile vibrations that can be felt by a user, perception of the presentation by the listener can be significantly improved owing to the effect of a multisensory stimulus resulting from the sound of the presenter, synchronized with a haptic stimulus delivered to the listener, where the haptic stimulus is a signal derived from the audio signal of the spoken presentation. In a basic case, the presence of a haptic stimulus can alert a listener that a speaker has begun a presentation, when the beginning of the presentation cannot be heard owing to background noise in a room.

Another example parses each word of a spoken presentation, and performs signal processing such as fundamental frequency extraction or low-pass filtering on each parsed word to generate a haptic cue definition for each parsed word. The stream of haptic cue definitions is used to actuate a haptic actuator, to transfer to a user a tactile stimulus with a frequency content that is related to the spoken presentation. As the presenter's voice modulates in frequency between words, so the frequency of the tactile stimulus experienced by the user changes, thus assisting the user to maintain focus on providing non-audible cues that can fill in gaps in the presentation.

Another aspect of the hardware and techniques discussed in the present specification concern monitoring and enhancing user attention to a speech or presentation by monitoring the pulse of a user. Academic research suggests a link between the heart rate variability (HRV) of a user, and attention maintenance. Accordingly, aspects of the hardware and techniques discussed herein concern using the user's HRV to monitor their attention to a speech or presentation, and, for example, upon detecting that a user's attention given to a speech or presentation is beginning to wane, to use haptic feedback as a response.

BRIEF DESCRIPTION OF THE DRAWINGS

Other characteristics will be apparent from the accompanying drawings, which form a part of this disclosure. The drawings are intended to further explain the present disclosure and to enable a person skilled in the art to practice it. However, the drawings are intended as non-limiting examples. Common reference numerals on different figures indicate like or similar features.

DETAILED DESCRIPTION

Figure 1:
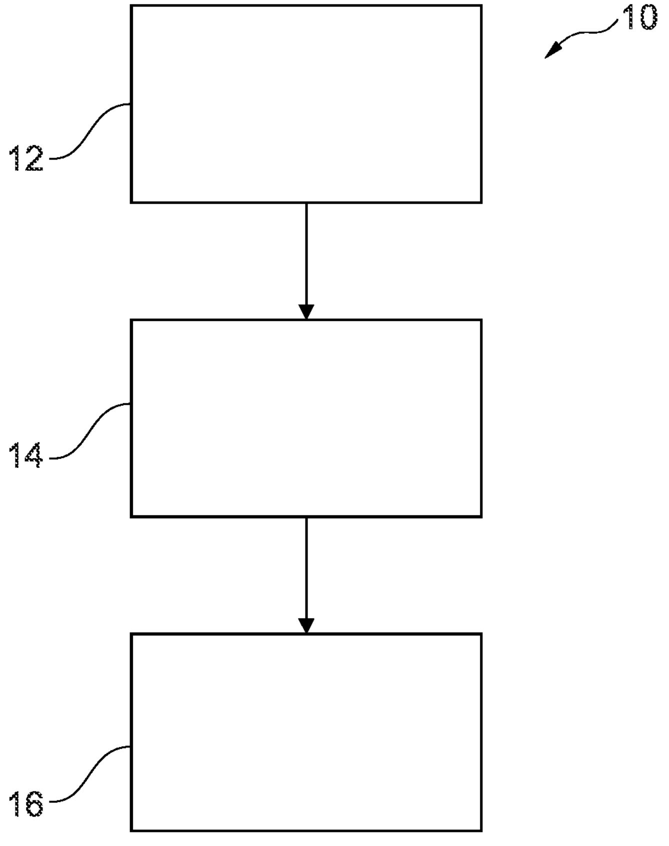
FIG. 1 schematically illustrates a computer-implemented method according to the first aspect.

This specification concerns hardware and techniques that enable users to understand, for example, verbal information in a noisy environment, and has applications in the education industry or in the business environment. Numerous studies demonstrate that transforming low-frequency speech signals into tactile vibrations provides a merging of information from different senses, known as multisensory enhancement, that can facilitate information processing. Accordingly, methods to generate multisensory stimuli in a range of environments, before presentation to a user, are of interest.

With the increasing availability of portable devices, and especially wearable devices, haptic and tactile feedback technologies have been miniaturised to a degree that they can fit into a small form-factor device. Examples of such devices are vibration motors, linear actuators, and piezoelectric crystals. Such devices can provide complex haptic feedback whilst using a low amount of power. An increasing number of consumers are interested in their fitness and well-being, and where portable and low-power heart rate sensors. Academic studies have demonstrated that there is a clear relationship between heart rate variability (HRV) of a user and the maintenance of attention of a user on a speech or lesson.

For example, the study "*Resting heart rate variability, attention and attention maintenance in young adults*" by Siennicka et. al, International Journal of Psychophysiology, Volume 143, September 2019, Pages 126-131 concluded that participants with a higher HRV had a constant level of attention on a specific subject, and therefore suggested that HRV can be used to create a metric that is related to a user's attention at a given moment. If, for example, a user is focused on a specific action or subject, and is then distracted, their HRV will change, thus indicating a loss of attention.

Other problems solved by the techniques and methods of the present specification are, therefore, to enable users to better understand audio presentations in a noisy physical environment and to facilitate the process of comprehending verbal information by inferring a user's attention level via the HRV and altering the strength of the haptic stimulus as a consequence of the measurement. By presenting a multisensory stimulus to a user comprising audio and haptic components, the multisensory reinforcement effect reduces apparent noise to a user trying to follow a presentation, and makes it easier for a user to maintain their attention on the presentation subject even in the event of a distraction.

A general explanation of the technique follows. Tactile feedback is generated by a device in physical contact with a user. In an example, the tactile feedback may be generated by a writing instrument 40 that has been supplemented by additional electronics and haptic actuator.

In a noisy environment, the user initiates the notetaking process in an attempt to capture the auditory information being shared by the presenter. The writing instrument 40 captures the speech signal from the presenter. A background process, operated by an embedded controller (processor) 36 of the writing instrument 40 in an example, performs audio analysis on each spoken word. In an example, the audio analysis extrapolates the fundamental frequency of each spoken word. A haptic feedback generator 34 that may be comprised in the writing instrument 40 and that is capable of generating frequencies below 500 Hz, for example, may be located in close proximity to the fingers of a user of the writing instrument 40. Human fingertips are sensitive enough that they can differentiate and identify a wide range of vibration frequencies.

The system described above is capable, in real time, to transfer specific vibration patterns that are correlated to each spoken word from the presenter at the user's fingertips. As described, the system generates the input stimuli responsible for multisensory enhancement, enabling a user to benefit from higher comprehension of verbal information in a noisy environment whilst also maintaining their attention on the subject of the presenter's speech. The combination of aural comprehension of the presentation and tactile feedback related to the frequency content of the words spoken during the presentation improve the understanding and memorisation process, even in a noisy environment.

As an extension to the concept, a device, in this example the writing instrument 40, is configured to obtain a signal representing the user's pulse. The embedded controller (processor) 36 of the writing instrument 40 is configured to perform signal processing on the signal representing the user's pulse in order to determine the heart rate variability HRV of the user. Based on a variation in the HRV, a surrogate metric representing an attention maintenance score of the user can be derived, because there is an association between higher resting HRV, and the attention given by a user to a subject at the time the resting HRV is measured.

Therefore, if the resting HRV reduces, this is one indication that a user is losing attention in the content of the spoken presentation. An aspect of the present specification concerns actuating the haptic actuator 34 of a user device such as a writing instrument 40 in order to alert the user to the loss of attention. In one example, the actuation comprises a generic pulse or plurality of pulses of the haptic actuator at a fixed frequency. In another example, the amplitude of the frequency stimulus derived from the presenter's voice can be increased or decreased according to the degree to which the resting HRV decreases or increases respectively. Hence, the present specification also provides a digital writing instrument 40 that can capture ambient audio containing speech and/or capture a user's HRV, and provide corresponding tactile feedback to the user.

FIG. 1 schematically illustrates a computer-implemented method according to the first aspect.

According to a first aspect, there is provided a computer-implemented method 10 for audio to tactile enhancement comprising:

- obtaining 12 audio data 18 comprising a sample of speech;
- generating 14 at least one haptic cue definition 22 by performing a first signal processing operation 39*c* on at least one portion of the audio data; and actuating 16 a haptic actuator 34 comprised in a user device 62 or a writing instrument 40 according to the at least one haptic cue definition 22.

In an example, the audio data 18 is captured using a microphone 33 of an apparatus 30 (to be discussed subsequently). The apparatus 30 may be embodied as, for example, a writing instrument 40, or another digital device such as a smartwatch, a mobile phone, laptop, a smart tablet, personal computer, netbook, and the like. Although a microphone 33 of user apparatus will experience substantially the same noise interference as the user's hearing system, is still possible to generate a viable haptic cue definition 22 based on audio data 18 obtained by a microphone 33 of the user apparatus, because sensitive microphones 33 exist and also signal processing (such as blind source separation) can be applied to the audio data 18 obtained by microphone 33 of the user apparatus.

In an example, the audio data 18 is uncompressed, in order to reduce the latency between obtaining a sample of speech and generating the at least one haptic cue definition 22.

Figure 10:
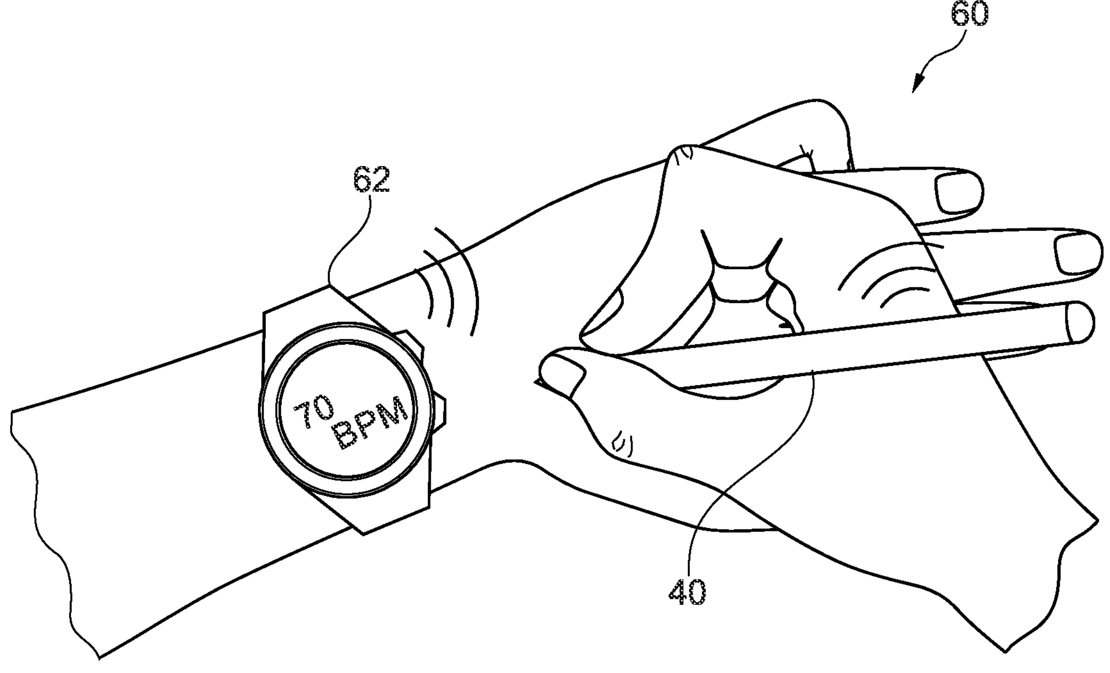
FIG. 10 schematically illustrates a system comprising a smart watch and a writing instrument.

In an example, the audio data 18 is obtained via a wireless communication interface 36*c* of an apparatus 30 (for example, writing instrument 40). The audio data 18, for example, can originate at a microphone 52 of a public address system 53 (as illustrated in FIG. 10, for example). The audio data 18 can be captured using an assistive listening technology such as an inductive hearing loop. In an example, an inductive hearing loop may be as based on the IEC 60118-4 standard. In an example, the audio data 18 is obtained from a public address system 53 using a packet-based protocol such as "Audio over IP" (AoIP).

In an example, the audio data 18 is captured from a sample of live speech. In an example, the audio data 18 is captured in real-time. In an example, the audio data 18 is obtained from a sample of recorded speech.

The first signal processing operation 39*c* generates a haptic cue definition 22 based on the frequency content of the audio data 18. Examples for generating the haptic cue definition 22 will be discussed below.

The actuation 16 of the haptic actuator is capable of generating a kinesthetic response that a user holding an apparatus 30 (such as a writing instrument 40) can feel in their fingers.

Figure 2:
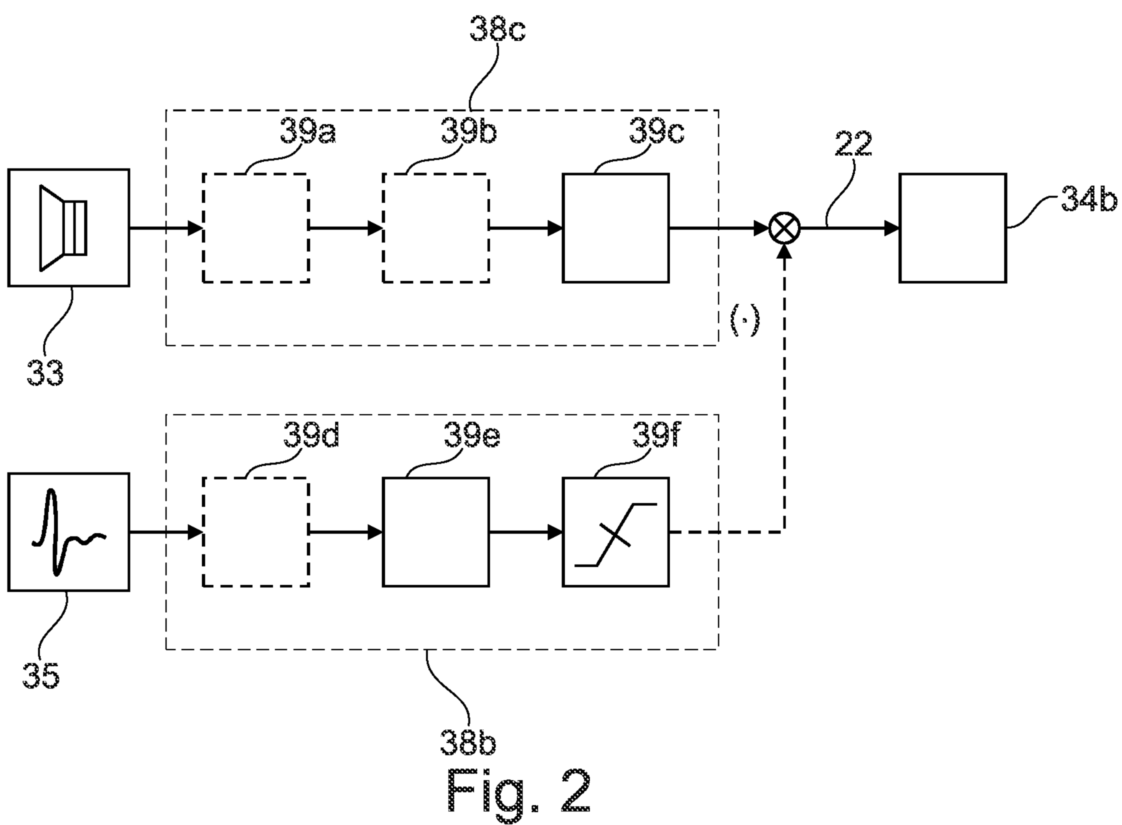
FIG. 2 schematically illustrates one example of signal processing.

FIG. 2 schematically illustrates one example of signal processing according to the present specification. Branch 38*c* is a speech to haptic algorithm (containing the first signal processing operation) and branch 38*b* is an attention monitoring algorithm (containing the second signal processing operation).

According to an example, obtaining the audio data 18 further comprises, prior to generating the at least one haptic cue definition 22:

extracting 20 the at least one portion of audio data 18 by pre-processing the audio data 18, wherein the pre-processing delimits 39*b* the at least one portion of audio data from a further portion of audio data by detecting a transition between a word, syllable, lexeme, or phoneme in the sample of speech comprised in the audio data.

For example, the speech to haptic algorithm 38*c* obtains audio data 18 from a microphone 33 (in an example, audio data 18 can be received from the wireless communication interface 36*c*). In an example, the step of audio pre-processing 39*a* (such as normalising the amplitude of the audio data 18 and/or removing high-frequency noise) and word delimiting 39*b* separates the audio data 18 into individual words, syllables, lexemes, or phonemes in the sample of speech. In this case, the fundamental frequency for each of the respective individual words, syllables, lexemes, or phonemes in the sample of speech may be calculated, leading to a more precise allocation of fundamental frequency to the correct individual word, for example.

The pre-processing stage 39*a* and word delimiter 39*b* may not be applied however, and in another example the fundamental frequency analysis can be applied according to a free-running sampling rate that is not related to the detection of individual words in the audio data 18. In this case, the fundamental frequency calculated, and upon which the haptic cue definition 22 is based, may be a freely varying frequency computed from the current audio data 18, and directly provided as a time-varying haptic cue definition 22.

According to an example, the first signal processing operation 39*c* generates the haptic cue definition 22 by obtaining the fundamental frequency of the at least one portion of audio data 18, and generating the at least one haptic cue definition 22 corresponding to the at least one portion of audio data based on the fundamental frequency of the portion of audio data.

Fundamental frequency analysis, also referred to as pitch detection, may be provided as time domain, frequency domain, and time-frequency domain algorithms. In an example, fundamental frequency analysis is performed by time domain autocorrelation on each portion of the audio data 18 of interest. Example algorithms are average magnitude difference function (AMDF), or average squared mean difference function (ASMDF). Frequency domain approaches involve, for example, cepstral analysis or Fourier analysis.

The fundamental frequency of human speech can vary from approximately 40 Hz for low pitched voices, to 600 Hz in respect of high-pitched voices.

According to an example, the first signal processing operation 39*c* generates the haptic cue definition 22 by low-pass filtering the at least one portion of audio data 18 generating the at least one haptic cue definition corresponding to the at least one portion of audio data based on the low-pass filtered portion of the portion of audio data 18.

In an example, the first signal processing operation comprises performing fundamental frequency analysis, to extract a fundamental frequency of a portion of the audio data. The haptic cue definition 22 is, in this example, a parametric definition comprising, for example, the fundamental frequency of a sine wave related to the fundamental frequency of a portion of the audio data.

In an example, the first signal processing operation comprises performing low-pass filtering on a portion of the audio data 18. For example, the first signal processing operation may apply a digital low-pass filter to the portion of the audio data 18. In an example, the digital low-pass filter has a cut-off frequency of one of 1 kHz, 900 Hz, 800 Hz, 700 Hz, 600 Hz, 500 Hz, 450 Hz, 400 Hz, 350 Hz, 300 Hz, 250 Hz, 200 Hz, 150 Hz, 100 Hz, 75 Hz, or 50 Hz. In an example, the digital low-pass filter is a finite impulse response (FIR) filter. In an example, the digital low-pass filter is an infinite impulse response (IIR) filter. In an example, the digital low-pass filter has a frequency characteristic defined by a Bessel response, a Chebyshev response, a Butterworth response, or an Elliptic response. As an example, the low-pass filter is an analogue filter situated between the microphone 33 and an analogue to digital converter of the apparatus 30.

The haptic cue definition 22 is, in an example, based on other extracted characteristics of the speech sample as well as the fundamental frequency. For example, the envelope of a word, fundamental frequency drift according to time, magnitude according to time, and the like may be encoded as additional aspects of the haptic signal definition 22.

In an example, a user may select, by a user interface software application, one or more frequency transmissions to apply when generating the haptic cue definitions 22 for each portion of the audio data 18. For example, a user may prefer a haptic signal based on speech synthesized using a high pitched voice, or a low pitched voice.

In a basic case, a haptic signal definition 22 is a sampled sine wave having a frequency corresponding to the fundamental frequency of an associated word in the audio data 18.

In an example, a null haptic cue definition 22 defining haptic feedback having zero amplitude is assigned to a portion of speech in which the sample of speech does not contain speech from the presenter.

The amplitude of the haptic cue definition 22 can, for example, be changed based on the influence of the attention monitoring algorithm 38*b* to be discussed subsequently. The haptic cue definition 22 is used to drive the haptic actuator 34*b*.

Figure 3:
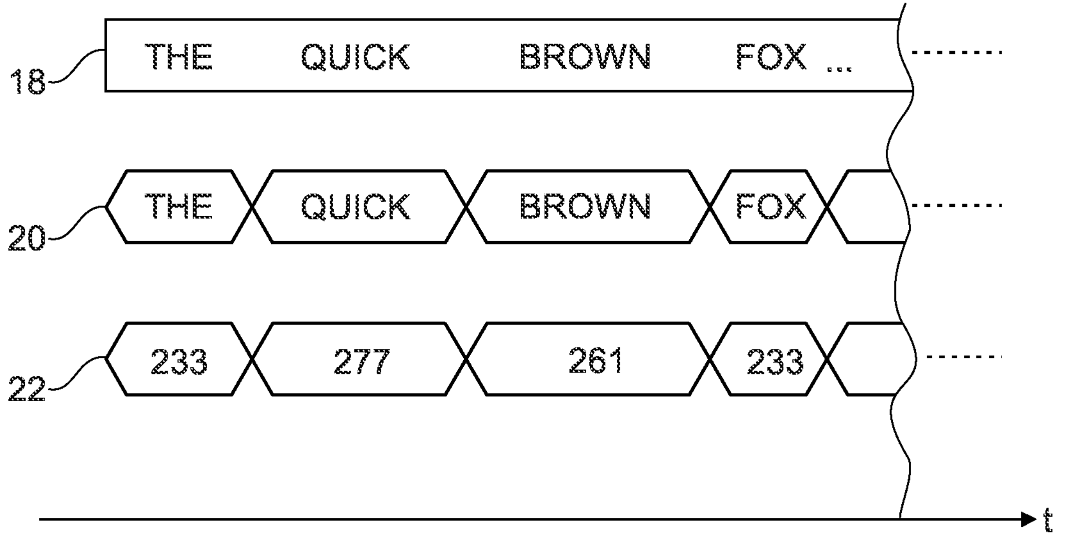
FIG. 3 schematically illustrates an example of converting an audio signal to a haptic cue.

FIG. 3 schematically illustrates an example of converting an audio signal to a haptic cue. For example, the audio data 18 may be an audio file or stream in ".WAV" format, sampled at 44.1 kHz, although a great many number of appropriate file formats for the audio file stream exist. A delimited speech sample 20 is generated, in this case by detecting individual words in the audio data 18. In the example of FIG. 3, fundamental frequency analysis is applied to each delimited word of the audio data 18, enabling a sequence of fundamental frequencies related to each delimited word to be provided as the basis for a sequence of four haptic cue definitions 22.

In an example, the haptic cue definition 22 is calculated, and transmitted to the haptic actuator 34*b* as actuation signals in near real-time from the audio data 18. This means that the time delay (latency) from the audio data 18 being received by the audio processing electronics 36*a*, and a user-discernible change in the haptic actuation performed by the haptic actuator 34*b*, is less than one of 500 ms, 400 ms, 300 ms, 200 ms, 100 ms, 50 ms, or 25 ms. Of course, the demands placed on the electronic controller 36 and associated audio processing electronics 36*a* will increase based on the desired latency between the reception of the audio data 18 and the haptic actuation performed by the haptic actuator 34*b*. A 500 ms delay may be attainable using a microprocessor, although a lower delay (such as 25 ms) would be more likely to require implementation using a Field Programmable Gate Array (FPGA) or an Application Specific Integrated Circuit (ASIC), for example. These delays are indicative and strongly depend on the type of fundamental frequency extraction algorithm used, and implementations details such as the degree of algorithmic parallelism employed.

The specification now discusses integration of heart rate variability detection with haptic audio enhancement.

Heart rate variability (HRV) is a physiological phenomenon of variation in the time interval between human heartbeats. It can be measured by the variation of beat to beat interval in milliseconds. Many techniques exist for measuring the HRV from measurable signals.

The European Society of Cardiology published a series of standard calculation techniques for HRV in the guidelines "*Heart Rate Variability—standards of measurement, physiological interpretation, and the clinical use*" by the task force of the European Society of cardiology and the North American Society of Pacing and Electrophysiology, published in the journal "Circulation", 0195-668X/96/030354 (1996).

As an example, heart activity signals can be obtained from electrocardiography (ECG), or photoplethysmography (PPG).

Figure 4:
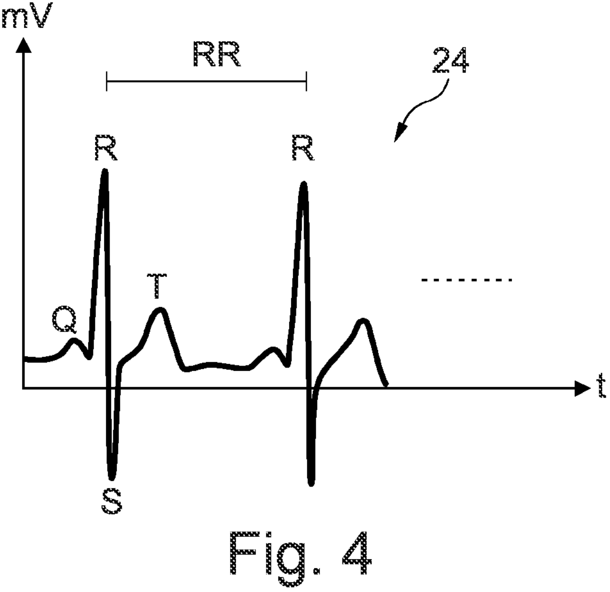
FIG. 4 schematically illustrates an example of an electrocardiogram (ECG) signal FIG. 5 schematically illustrates an example of a photoplethysmography (PPG) signal.

FIG. 4 schematically illustrates an example of an electrocardiogram (ECG) signal 24. An electrocardiogram is representation of voltage versus time of the electrical activity of the heart, measured by electrodes placed on the skin. For accurate measurement of the ECG, specialised cardiac monitoring leads can be affixed to the chest of a user by adhesive. However, the detection of reliable ECG signals at other points on the surface of the human body have been demonstrated, and some smartwatches provide ECG detection at the wrist. An ECG signal of healthy human typically comprises a QRS complex, followed by a T wave. FIG. 4 schematically indicates the locations of the Q, R, S, and T points on a typical sample of an ECG. The Q, R, S, and T points are directly related to electrical polarisations and depolarisations occurring in a human heart.

Signal processing may be performed to derive the time delay between successive R peaks, to thus provide the so-called RR interval. Calculating statistical measures such as the variance and/or standard deviation of a sequence of RR intervals provides one accepted measure of the HRV. Accordingly, in an example, an apparatus 30 or writing instrument 40 are provided with electrodes capable of measuring the ECG from the fingers or hand of a user of an apparatus 30 or writing instrument 40, and the heart rate variability is calculated from the ECG so obtained.

Figure 5:
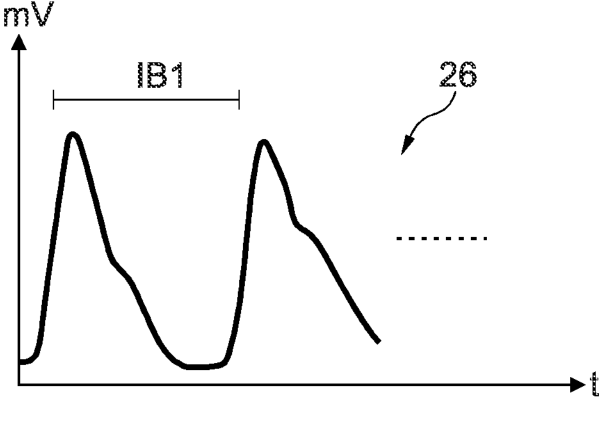

FIG. 5 schematically illustrates an example of a photoplethysmography (PPG) signal 26. For comparison, the PPG signal 26 is illustrated in time synchrony to the ECG signal 24 of FIG. 4. The principle of photoplethysmography is that a light source is placed on one side of a blood carrying vessel, or a microvascular bed of tissue exposed to pressure from cardiac expansion and relaxation. A photodetector is placed on the other side of a blood carrying vessel, or a microvascular bed of tissue such that the photodetector measures light from the light source, and an accompanying attenuation caused by the propagation of light through the blood carrying vessel, or a microvascular bed of tissue.

During a systolic phase, a heartbeat contracts the heart, such that after a given time delay the blood carrying vessel, or microvascular bed of tissue through which the light travels, experience engorgement and thus cause greater attenuation to the light. During a diastolic phase, draining of fluid from the blood carrying vessel or microvascular bed of tissue leads to a lesser attenuation of the light. Accordingly, an example of a resulting periodic PPG signal 26 is illustrated in FIG. 5.

The inter-beat interval IBI is an acceptable proxy for the RR interval of an ECG signal, and variations of the IBI can, likewise, be used to compute the HRV. This is discussed, for example, in the book chapter "*Heart Rate Variability Recording System Using Photoplethysmography Sensor*" by Noor Aimie-Salleh et. al, in "Autonomic Nervous System Monitoring" (Theodoros Aslanidis, Ed.), DOI: 10.5772/intechopen.89901, Published: Nov. 29, 2019.

Figure 6:
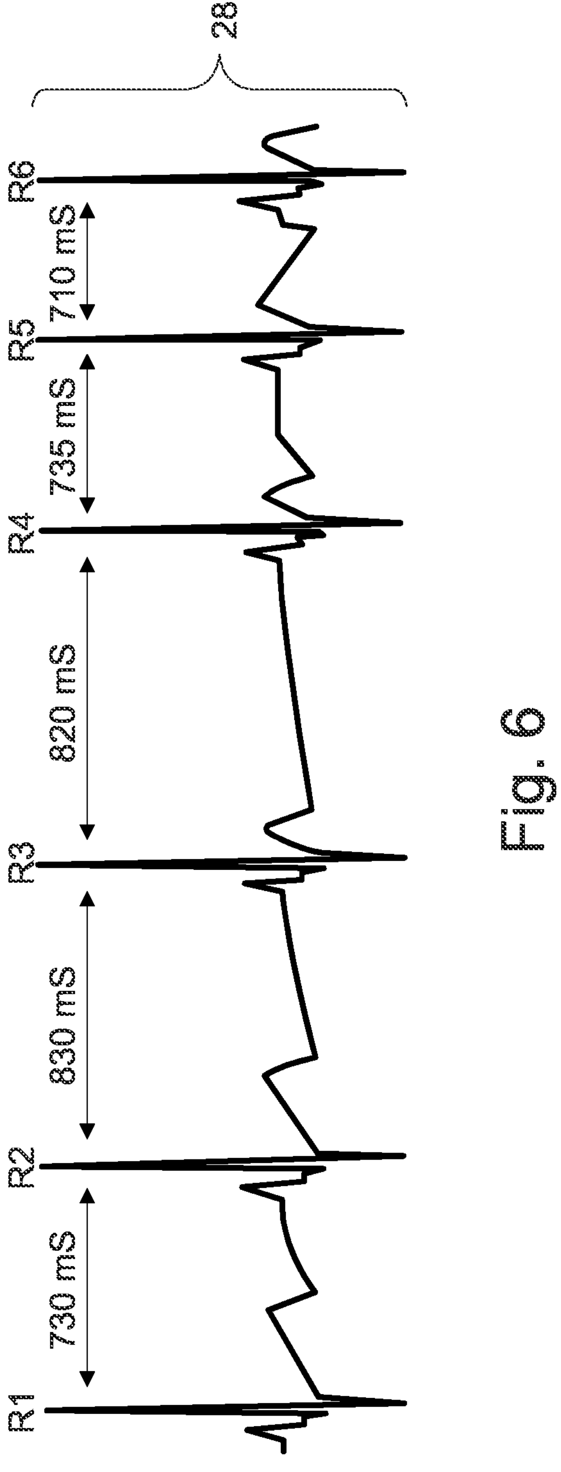
FIG. 6 schematically illustrates an example of heart rate variability (HRV) as measured in an electrocardiogram (ECG) signal.

FIG. 6 schematically illustrates an example of heart rate variability (HRV) 28 as measured in an electrocardiogram (ECG) signal.

According to an example, the computer-implemented method further comprises:

obtaining a pulse signal representing a pulse of a user of the user device 62 or the writing instrument 40, wherein the pulse signal is obtained substantially simultaneously with obtaining the audio data 18; and applying a second signal processing operation 39*e* to the pulse signal, wherein the second signal processing operation calculates a heart rate variability signal of the user.

In an example, the pulse signal is obtained from an electrocardiogram. In an example, the pulse signal is obtained from PPG (optical pulse detection).

In an example, the second signal processing operation 39*e* applies the Pan and Tomkins algorithm to a pulse signal obtained using an electrocardiogram to obtain the HRV.

In an example, the second signal processing operation 39*e* obtains an electrocardiogram. The electrocardiogram is bandpass filtered to remove noise. The resulting signal is applied to a derivative filter, or similar, to obtain slope information of the QRS complex. The resulting signal is squared and applied to a peak detector. The signal is thresholded and applied to a moving average filter, as discussed in FIG. 3 of the "*Heart Rate Variability Recording System Using Photoplethysmography Sensor*" above. This is an example of how an ECG signal is converted into a precursor signal for HRV analysis.

In an example, the second signal processing operation 39*e* applies the Slope Sum Function (SSF) to a pulse signal obtained using Photoplethysmography (optical pulse detection) to obtain the HRV. This is an example of how a PPG signal is converted into a precursor signal for HRV analysis.

As one example, the approach of FIG. 3 of the "*Heart Rate Variability Recording System Using Photoplethysmography Sensor*" can be applied to either of the precursor signals obtained from an ECG or PPG. A normal to normal interval (NN interval) is computed, with outliers in the signal being removed. In an example, computing the standard deviation of a sequence of NN intervals yields the HRV.

Momentarily referring back to FIG. 2, signal branch 38*b* represents an attention monitoring algorithm. Pulse signal processing 39*d* corresponding, for example, to the Pan and Tomkins or SSF approaches discussed above may be applied, based on whether or not the pulse signal is obtained by ECG or PPG. Of course, other pulse signal processing approaches can be applied at 39*d* as well. The HRV is computed at step 39*e*. Finally, a change in the HRV is monitored at step 39*f* is a heart rate variability criterion.

According to an example, the computer-implemented method further comprises:

monitoring a change of the heart rate variability signal of the user; and when the change of the heart rate variability signal of the user changes, altering the at least one haptic cue definition 22.

According to an example, if the heart rate variability signal of the user decreases such that it meets a criterion, the at least one haptic cue definition is altered, to thus cause an increase in the amplitude of the actuation of the haptic actuator 34*b*.

According to an example, if the heart rate variability signal of the user increases such that it meets a criterion, the at least one haptic cue definition is altered, to thus cause a decrease in the amplitude of the actuation of the haptic actuator 34*b*.

Of course, the change in the haptic cue definition 22 is not limited to a change in amplitude. The haptic cue definition 22 could, alternatively or in addition, be qualitatively changed, such that a strobing effect is generated when it is determined that a user has lost attention.

A wide range of heart rate variability criteria can be applied. For example, when the HRV falls below a predefined, or user-specified threshold, a process can be triggered to increase the amplitude of the at least one haptic cue definition 22. In an example, the at least one haptic cue definition 22 is changed suddenly according to a step function. Such mode is capable of quickly alerting a user, via haptic stimulus, to the fact that they are losing attention in a speaker.

In an example, the at least one haptic cue definition 22 is changed as a linear proportion of the degree to which the HRV has fallen below the predefined or user specific threshold. In other words, a greater deviation of the HRV below the predefined or user specific threshold corresponds to a greater increase in the haptic stimulus applied to the user by the haptic actuator. Such a mode is more gradual, and likely to be less intrusive to a user whose heart rate variability is more unpredictable.

In an example, the criterion is whether or not the heart rate variability signal taken at a present time instant has fallen below a percentage of a moving average during a given time window immediately previously to the present time instant.

For example, the time window may compare an instant (present) value of the heart rate variability with the average heart rate variability calculated over the previous 1 second, 2 seconds, 3 seconds, 4 seconds, 5 seconds, 10 seconds, 20 seconds, 30 seconds, 40 seconds, 50 seconds, 1 minute, 2 minutes, 5 minutes, or 10 minutes.

The criterion is satisfied if an instant (present) heart rate variability drops below 0.1%, 0.5%, 1.5%, 2%, 2.5%, 3%, 4%, 5%, 6%, 7%, 8%, 9%, or 10% of the average heart rate variability calculated over the time window immediately previously to the present time instant. In other words, the decrease in heart rate variability is a proxy for the attention of a user on a presentation. A skilled person will appreciate that many other statistical criteria could be used to determine whether, or not, the heart rate variability contains artefacts indicative of a loss of attention.

According to an example, the computer-implemented method further comprises:

monitoring a change of the heart rate variability signal of the user; and when the change of the heart rate variability signal of the user increases, altering the at least one haptic cue definition 22.

In an example, the criterion is whether or not the heart rate variability signal taken at a present time instant has increased above a percentage of a moving average during a given time window immediately previously to the present time instant.

For example, the time window may compare an instant (present) value of the heart rate variability with the average heart rate variability calculated over the previous 1 second, 2 seconds, 3 seconds, 4 seconds, 5 seconds, 10 seconds, 20 seconds, 30 seconds, 40 seconds, 50 seconds, 1 minute, 2 minutes, 5 minutes, or 10 minutes.

The criterion is satisfied if an instant (present) heart rate variability increases above 0.1%, 0.5%, 1%, 1.5%, 2%, 2.5%, 3%, 4%, 5%, 6%, 7%, 8%, 9%, or 10% of the average heart rate variability calculated over the time window immediately previously to the present time instant. In other words, the increase in heart rate variability is a proxy for the improved attention of a user on a presentation. A skilled person will appreciate that many other statistical criteria could be used to determine whether, or not, the heart rate variability contains artefacts indicative of a gain of attention.

In this example, in the case that the heart rate variability increases above a predetermined criterion, the at least one haptic cue definition 22 is attenuated or reduced in magnitude, or altered such that resulting haptic cues are less prominent, because the user has regained attention on the presentation.

Although, according to the technique of this specification, it is not necessary to directly track a metric defining the attention of a user, such metrics do exist. For example, in the paper "*Resting heart rate variability, attention and attention maintenance in young adults*", by A Siennicka et. al, in the international journal of Psychophysiology, 2019 September; 143:126-131, doi: 10.1016/j.ijpsycho.2019.06.017, Epub 2019 Jun. 27, an example of an attention maintenance test is provided, in which the D2 test of attention is discussed.

According to an example, the user device 62 is a smartwatch or fitness band comprising a haptic actuator. Modern smartwatches and fitness bands are equipped with ECG and/or PPG monitoring transducers, as well as wireless communication interfaces capable of transferring pulse signals to an apparatus 30 or a writing instrument 40, for example.

A specific example user method is now provided, although skilled person will appreciate that there are many variations.

Once a presenter has begun a presentation including auditory component, a user of an apparatus 30 such as a writing instrument 40 begins a notetaking process in synchrony with the presenter. Audio data 18 from the presenter can be obtained, either from a microphone 33 incorporated in the apparatus 30 or writing instrument 40, or via a wireless communication network as part of a public address system 53. Software operated by a processor of the apparatus 30 or writing instrument 40 converts, for example, each word spoken by the presenter to a vibration pattern defined by haptic cue definition 22. The haptic cue definition 22 corresponding to each word is used by the apparatus 30 or writing instrument 40 to actuate a haptic actuator 34*b*. This induces a haptic stimulus in, for example, a finger of the user based on, for example, a fundamental frequency analysis of a respective word. The haptic stimulus is generated as quickly as possible, and ideally almost simultaneously, with the time at which the audio data 18 is obtained, although human nervous system can tolerate some delay, such as 10 ms or 100 ms between hearing the word, and feeling the multisensory kinesthetic stimulus.

Simultaneously, the apparatus 30 or writing instrument 40 measures a pulse signal of the user using ECG or PPG, and from this derives the heart rate variance of the user. Heart rate variance is a proxy for the attention level of the user. In an example, when the heart rate variance drops, this is a proxy for a declining attention level of the user. If the attention level is deemed to have dropped below a predefined threshold, the apparatus 30 or writing instrument 40 increases the amplitude of the haptic cue defined in the haptic cue definition 22, such that when the haptic actuator 34*b* is actuated, the amplitude of the vibrations transferred to the user is increased. The increase in vibration is perceived by the user and via multisensory enhancement, the user's attention on the presentation is maintained. Although the aforementioned procedures can take place as a background process without active user involvement, a user interface that can be accessed via the apparatus 30 or writing instrument 40 may enable the user to adjust the style of haptic intervention generated when attention is deemed to be lacking, for example. In addition, a user interface may enable user to perform a calibration or familiarization run, to ensure that the amplitude of the haptic signals is not boosted unnecessarily.

Figure 7:
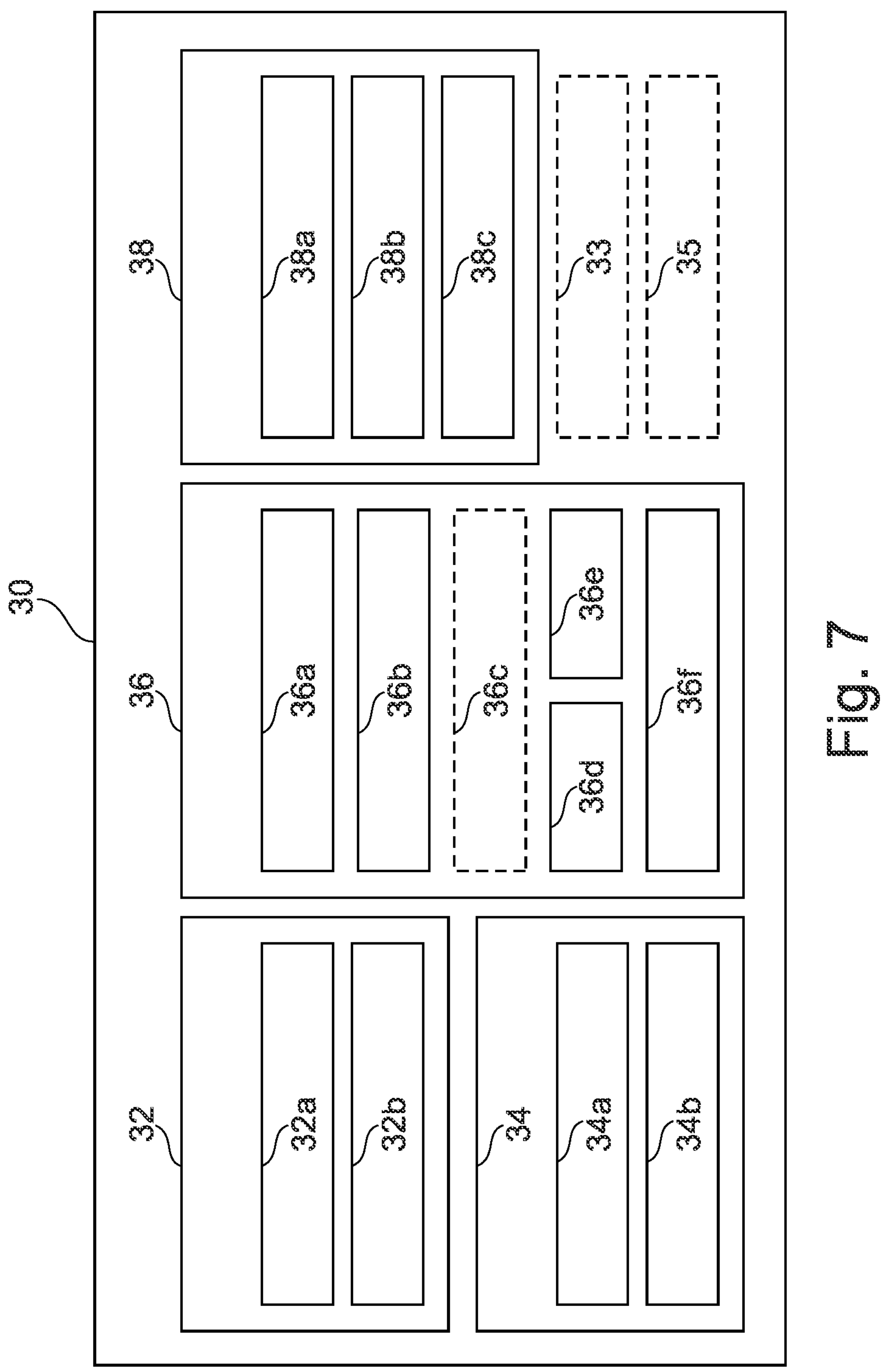
FIG. 7 schematically illustrates an apparatus according to an example.

FIG. 7 schematically illustrates an apparatus 30 according to an example.

The apparatus 30 may be specifically embodied as a writing instrument 40, although skilled person will appreciate that the hardware and circuitry to be discussed can be implemented on a wide range of devices, such as a smart phone, smartwatch and the like.

According to an example, the apparatus 30 is a smartwatch comprising a pulse sensor 35 and/or a haptic actuator 34*b*.

According to an example, the apparatus 30 is a fitness band smartwatch comprising a pulse sensor 35 and/or a haptic actuator 34*b*.

According to an example, the apparatus 30 is a smart finger ring smartwatch comprising a pulse sensor 35 and/or a haptic actuator 34*b*.

According to an example, the apparatus 30 is a haptic glove smartwatch comprising a pulse sensor 35 and/or a haptic actuator 34*b*.

The apparatus 30 comprises a power supply 32. The power supply 32 comprises energy storage 32*a* and a charging system 32*b*. Energy storage 32*a* is, for example, a battery.

In an example, the apparatus 30 comprises a microphone 33. The microphone may be a moving coil microphone, a condenser microphone, an electret microphone, ribbon microphone, crystal microphone, ceramic microphone, a carbon microphone, or a MEMs (micro electromechanical) microphone. When the microphone 33 is integrated into an apparatus 30 embodied as a writing instrument 40, the location of the microphone 33 should be in the portion of the writing instrument 40 that is not covered by the user's fingertips in use, such as the distal end D of the writing instrument 40.

The apparatus 30 comprises a haptic feedback generator 34. The haptic feedback generator 34 comprises interface electronics 34*a* and haptic actuator 34*b*. The haptic feedback generator 34 is capable of receiving digital instructions from the controller 36 and converting them into vibrations that can be felt by user of the apparatus 30. In an example where the apparatus 30 is embodied in writing instrument 40, the location of the haptic actuator 34*b* is as close to the user's fingertips on the writing instrument 40 as possible.

The haptic actuator 34*b* generates mechanical energy in the form of vibrations that can be felt by the user in an example, the haptic actuator 34*b* is configured to generate vibrations in the range of 0 to 500 Hz with a controllable amplitude and or envelope. In an example, the haptic actuator 34*b* is configured to generate narrowband, such as sinusoidal vibrations. In an example, the haptic actuator 34*b* is configured to generate broadband vibrations characterised by a frequency spectrum having a plurality of frequency components.

In an example, the haptic actuator 34*b* is a rotary motor connected to a vibration cam. In an example, the haptic actuator haptic actuator 34*b* is a linear vibration motor. In an example, the haptic actuator 34*b* is a piezoelectric vibration motor. Other types of vibration generators can be used without loss of generality.

The interface electronics 34*a* comprise motor drivers and firmware required for converting drive instructions from the controller 36 into signals appropriate for driving the haptic actuator 34*b*.

In an example, the apparatus 30 comprises a pulse sensor 35.

In an example, the pulse sensor 35 is an electrical heart rate sensor configured to capture ECG signals from a user. For example, when embodied as a writing instrument 40, a pulse sensing region 45 of the writing instrument 40 is provided with electrodes suitable for receiving ECG signals contacting the fingers or first interdigital space of the user's hand.

In an example, the pulse sensor 35 is an optical heart rate sensor disposed at a point on the apparatus 30 that the usual contact, in use. For example, when embodied as a writing instrument 40, a pulse sensing region 45 of the writing instrument 40 is provided with pulse sensing region 45 comprising optical sensors and analogue electronics suitable for obtaining optical pulse signals, such as PPG signals from the user's fingers.

In another example, the pulse sensor 35 does not need to be incorporated in the apparatus 30 or the writing instrument 40. A user may wear a separate user device 62, an example a smartwatch or a fitness band, configured to measure the pulse and/or calculate a heart rate variability of user. In this case, the user device 62 is configured to communicate the pulse and/or heart rate variability of user to the apparatus 30 via a wireless communication interface 36*c*.

The controller 36 comprises analogue and digital electronic components which enable the apparatus 30 to function. The controller 36 comprises audio processing electronics 36*a*. In an example, the audio processing electronics 36*a* is configured to receive an analogue or digital audio signal from the microphone 33. In a further example, the audio processing electronics 36*a* is configured to receive a digital audio signal via a wireless communication interface 36*c* (for example, in a case where digital audio is received from the public address system 53 of a lecture theatre, or from a microphone incorporated in a network connected mobile device located more closely to a presenter).

The audio processing electronics 36*a* comprises analogue and/or digital components capable of performing the function of, for example, the audio pre-processing stage 39*a*, the word delimiter 39*b* and the haptic cue generator 39*c* (first signal processing operation) illustrated in FIG. 2. The audio pre-processing stage 39*a* may be implemented as a mixture of analogue and digital components, and also comprises an analogue to digital converter. The word delimiter 39*b* and the haptic cue generator 39*c* are implemented as digital signal processing algorithms in processor 36*d* or a separate digital signal processor (not illustrated).

The controller 36 comprises pulse monitoring electronics 36*b* capable of implementing the functions such as pulse signal pre-processing 39*d*, heart rate variability computation 39*e*, and applying a heart rate variability criterion 39*f*. The pulse signal pre-processing stage 39*d* may be implemented as a mixture of analogue and digital components, may also comprise an analogue to digital converter or time-indexed peak detector. The heart rate variability computation 39*e* and heart rate variability criterion 39*f* are implemented, for example, as digital signal processing operations either using the processor 36*d* or a separate digital signal processor.

For example, the heart rate variability computation 39*e* is configured to measure a plurality of time delays between successive peaks of an ECG or PPG signal. The heart rate variable computation 39*e* is configured to compute a statistical measure, such as standard deviation, of the time delays. The statistical measure is a form of heart rate variability metric, and can be used as a proxy for attention monitoring of a user of the apparatus 30.

In an example, the controller 36 comprises a wireless communication interface 36*c*. For example, application software of the apparatus 30 or related writing instrument 40 may be provided to communicate data, or to receive software or firmware updates from a wireless network. In some embodiments, a software module 38 of the apparatus 30 or related writing instrument 40 is configured to receive audio data 18 and pulse measurement data from remote devices. For example, the software module 38 of the apparatus 30 may receive audio data 18 from a public address system 53. The software module 38 of the apparatus 30 may receive pulse measurement data from a further user device 62 such as a smartwatch. In this case, such data is communicated via the wireless communication interface 36*c*.

The wireless communication interface 36*c* comprises a chipset capable of performing bidirectional data communication with external devices such as user device 62/or a network interface such as a router.

For example, the wireless communication interface 36*c* comprises Bluetooth™, Bluetooth Low Energy™, Wi-Fi™ (802.11a, b, g, n, ac, ad), Wireless USB, UMTS, LTE, or ZigBee™ interfaces, as implemented by associated chipsets.

The controller 36 further comprises a processor 36*d*. The function of the processor 36*d* is to perform the memory read write, input/output read-write, and computation functions necessary to enable the apparatus 32 function. The processor 36*d* coordinates hardware of the apparatus 30 such that the appropriate measurements and user requests are recognised and executed accordingly. The processor 36*d* executes the operating system 38*a* and associated applications. The processor 36*d* can comprise a microcontroller or microprocessor suitable for low energy, real-time processing such as an ARM™ Cortex A510, although a skilled person will be able to use other microprocessors and circuitry.

The controller 36 further comprises a memory 36*e*, comprising a combination of volatile and non-volatile memory. In use, the processor 36*d* is configured to read from memory 36*e* machine readable instructions, and to execute the machine readable instructions that instantiate and run a software module 38.

The process of generating haptic cue definitions 22 based on received audio data 18 and actuating an associated haptic actuator 34*b*, and the process of computing a heart rate variability metric and altering the haptic cue definitions 22 based on the computed heart rate variability metric can all be performed as background tasks without user intervention.

However, some aspects of the operation of the apparatus 30 may benefit from user configuration. Therefore, in an example, the controller 36 further comprises a user interface 36*f*. When the apparatus 30 is embodied as a writing instrument 40, the user interface 36*f* is an "on/off" switch on the body 42 of the writing instrument, for example. A button, a rotatable encoder wheel, or a linear slider as an example of a user interface that can be connected to the controller 36 and used for volume adjustment or adjustment of a baseline magnitude of the haptic cue definition 22, for example.

In another example, the apparatus 30 comprises a screen capable of displaying a menu-based user interface 36*f*, enabling more sophisticated interaction and programming with apparatus 30. For example, the apparatus 30 may display to a user a graph representing a proxy of attention maintenance over the duration of a lecture, for example.

A skilled reader will appreciate that the software module 38 is not a hardware feature of the apparatus 30, but that when instantiated by the operation of the processor 36*f*, performs relevant functions.

In operation, the software module 38 comprises an operating system 38*a*. This operating system 38*a* managers the devices hardware, software resources, and provides common services for application-specific algorithms. An embedded operating system such as "Linux embedded", or "Mbed OS" may be used as the operating system, although many alternatives exist.

In operation, the software module 38 comprises an attention monitoring algorithm 38*b*. The attention monitoring algorithm 38*b* is a background process (in other words, it typically operates for the entire time that the user has enabled attention based haptic feedback in the apparatus 30) responsible for utilising data from the pulse sensor 35, and generating a heart rate variability figure of merit. The attention monitoring algorithm 38*b* may apply the heart rate variability figure directly as a figure of merit of attention maintenance, or the attention monitoring algorithm 38*b* may perform further transformations, signal processing, or lookup table operations to transform heart rate variability into an attention monitoring figure of merit.

In an example, the attention monitoring algorithm 38*b* is configured to operate a calibration sequence, where the user is instructed to pay attention to a sample task (such as the D2 test) whilst the apparatus 30 is calibrating itself to generate a baseline attention maintenance score based on a baseline heart rate variability figure of merit. The criterion on which to determine whether or not a user is losing attention can be based on the baseline heart rate variability figure of merit, for example.

In operation, the software module 38 comprises a speech to haptic algorithm 38*c*. The speech to haptic algorithm 38*c* is a background process (in other words, it typically operates for the entire time that the user has enabled attention based haptic feedback in the apparatus 30). In an example, the speech to haptic algorithm 38*c* is configured to analyse the frequency components of the audio data 18 in real-time. In an example, the speech to haptic algorithm 38*c* is configured to perform fundamental frequency analysis to determine the original amplitude and fundamental frequency of the audio data 18 (or a portion of the audio data 18 related to a word, syllable, lexeme, or phoneme). The resulting signal is converted to a haptic cue definition 22 as described previously.

A haptic cue definition 22 for a captured word, syllable, lexeme, or phoneme is transmitted to the haptic actuator 34*b* in real time, or as quickly as possible, so that the relevant vibration can be can kinesthetically experienced by a user in close temporal proximity to the sampled speech used to generate the haptic cue definition 22 and associated haptic stimulus generated by the haptic apparatus 34*b*.

In the example, the heart rate variability at a given time instant, or a proxy attention maintenance score calculated from the heart rate variability, can be used by the apparatus 30 to vary the amplitude of the output vibrations when the attention monitoring algorithm 38*b* determines that the user has lost their attention, in order to attempt to bring the user's focus back, or to alert the user to the fact that their attention is drifting. In an example, when the attention monitoring algorithm 38*b* determines that the user's focus has been restored, the haptic cue definitions 22 are altered to reduce, for example, the amplitude of the related vibrations generated by the haptic actuator 34*b*. In the example, a user interface element such as a slider or screen display element can be used to adjust the haptic cue definitions 22.

Figure 8:
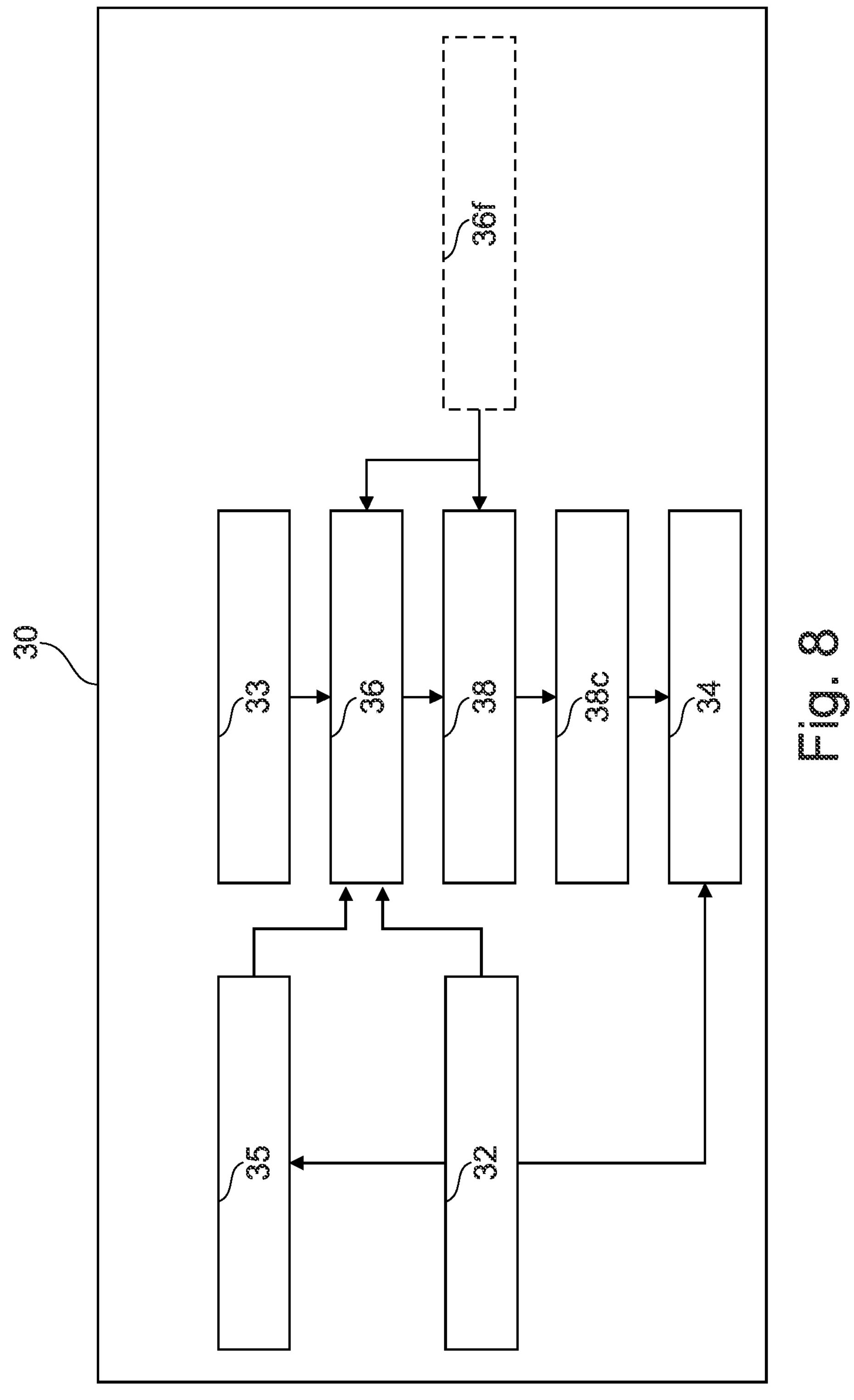
FIG. 8 schematically illustrates process flow in the apparatus according to an example.

FIG. 8 schematically illustrates process flow in the apparatus 30 according to an example.

According to a second aspect, there is provided a writing instrument 40 for audio to tactile enhancement, comprising a processor 36*d*, and a haptic actuator 34*b*.

The processor 36*d* is configured to obtain audio data 18 comprising a sample of speech, to generate at least one haptic cue definition 22 by performing a first signal processing operation on at least one portion of audio data, and to actuate the haptic actuator 34*b* according to the at least one haptic cue definition 22.

According to an example, the writing instrument comprises a microphone 33. The processor 36*d* is configured to obtain audio data from the microphone 33.

According to an example, the writing instrument further comprises a wireless communication interface 36*c*. The processor 36*d* is configured to obtain audio data 18 via the wireless communication interface 36*c*.

According to an example, the writing instrument further comprises a pulse sensor 35. The processor 36*d* is configured to obtain a pulse signal of a user of the writing instrument 40 by measuring a pulse of a user of writing instrument using the pulse sensor 35 substantially simultaneously with obtaining the audio data 18. The processor 36*d* is configured to apply a second signal processing operation 39*e* to the pulse signal, wherein the second signal processing operation calculates the heart rate variability of the user.

According to an example, the processor 36*d* is further configured to monitor a change of the heart rate variability of the user of the writing instrument 40. The processor 36*d* is configured to alter the at least one haptic cue definition 22 to cause a corresponding increase in amplitude of the actuation of the haptic actuator 34*b*, when the change of the heart rate variability of the user meets a criterion.

Figure 9:
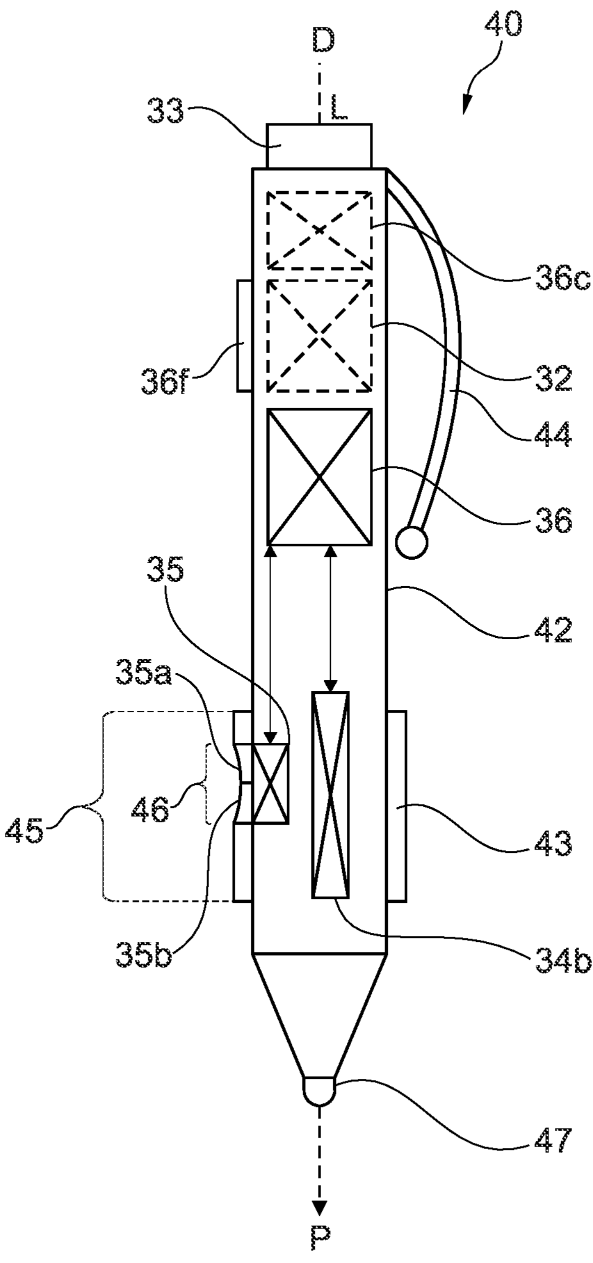
FIG. 9 schematically illustrates an example of a writing instrument.

FIG. 9 schematically illustrates an example of a writing instrument 40. The writing instrument 40 comprises the elements described in the foregoing description of the apparatus 30, although some elements are omitted from FIG. 9 for the sake of clarity. Like reference numerals in FIG. 9 denote the same elements as described previously.

In the example of FIG. 9, the writing instrument 40 comprises a body 42. In an example, the body 42 has a circular, ovular, square, rectangular, pentagonal, hexagonal, or heptagonal cross-section along at least a portion.

The form-factor of the body portion 42 can change along the longitudinal axis L of the writing instrument 40 to accommodate ergonomic variations or to enhance user comfort, for example (not illustrated).

A proximal end P of the writing instrument is closer to a writing surface, in use. A distal end D of the writing instrument is further from the writing surface compared to the proximal end P, in use. A longitudinal axis L is provided between the proximal end P and the distal end D. The writing instrument comprises a nib 47 at the proximal end. The nib 47 can be a felt tip, pencil, or fountain pen nib, or a plastic stub suitable for use with a digital writing tablet.

In an example, the total length of the writing instrument 40 in the longitudinal direction L is between 50 mm and 200 mm, and specifically 140 mm. In an example, when the writing instrument 40 has a circular cross-section, the maximum diameter of the writing instrument 40 is in the range of 6 mm to 20 mm, and specifically 9 mm. The body portion 42 of the writing instrument 42 can, for example, comprise polystyrene or polypropylene.

In the illustrated example, the external surface of the writing instrument 40 comprises, near to its distal end D, a pen clip 44 for facilitating attachment to a user's pocket, for example. The writing instrument 40 can comprise, near to the proximal end, a grip 43 enabling secure grip of the device whilst still being capable of transmitting haptic sensations to a user. The user grip can be moulded to achieve an ergonomic match with a typical user profile, to enhance writing comfort. In an example, the haptic actuator 34*b* is disposed within the body 42, and proximate to the grip 43, to enable an optimum transfer of haptic sensation to a user. In an example, a microphone 33 is located at, or near, the distal end of the writing instrument 40.

The writing instrument 40 comprises a pulse sensing region 45. The pulse sensing region 45 is disposed on the body 42 so as to be touched by a user, when the writing instrument 40 is in use. In an example, a case where optical pulse detection is applied, the pulse sensing region 45 comprises a skin contact portion 46 set into the grip 43. The pulse sensor 35 comprises a first portion 35*a* and a second portion 35*b*. For example, the first portion 35*a* comprises a light emitter, such as an infrared light-emitting diode. The second portion 35*b* comprises a light detector tuned to the frequency of the light emitter, such as a photo transistor or photodiode. The first portion 35*a* and second portion 35*b* are, for example, formed from polycarbonate capable of transmitting light. The skin-facing surface of the first portion 35*a* and second portion 35*b* may be lensed or comprise a concave region to form an appropriate interface with the skin of a user.

The controller 36, power supply 32, and wireless communication interface 36*c* along with ancillary electronics may be mounted on a base board (not shown) inside the body 42. In an example, a user interface 36*f* is comprised on an external surface of the body 42. The user interface 36*f* can be one or a combination of a switch, a rotary dial, a light emitting diode display, an LCD or OLED display, and the like, dependent on the degree of user interaction required.

According to a third aspect, a system 60 is provided. The system comprises a writing instrument 40 according to the second aspect, or its examples. The system further comprises a user device 62 comprising a pulse sensor 35 and a wireless communication interface. The user device 62 is configured to measure a pulse signal of a user of the user device using a pulse sensor and to compute a heart rate variability signal of the user based on the pulse signal. The user device 62 is configured to transmit the heart rate variability signal of the user to the writing instrument 40 via a wireless communication interface of the user device 62.

Therefore, existing user equipment (user device 62) can be used, via existing application programming interfaces (APIs), Web services, or short range wireless links, to provide a user pulse signal, and/or to obtain audio data 18.

FIG. 10 schematically illustrates a smart watch and a writing instrument.

In this case, the user device 62 is in the form of a smartwatch that is worn by the same user as the user of the writing instrument 40. The smartwatch is configured to measure the pulse of the user using an optical or electronic sensor. In one variation, the smartwatch computes heart rate variation and communicates the heart rate variability HRV to the writing instrument 40. In another variation, the smartwatch communicates the pulse of the user to the writing instrument 40, and the writing instrument 40 computes the heart rate variability HRV. In an example, a haptic generator of the user device 62 (such as a smartwatch) can be used to deliver the haptic signal to the user.

Accordingly, a user device 62 that is already owned by the user can be used to implement aspects of a multisensory stimulus device.

Figure 11:
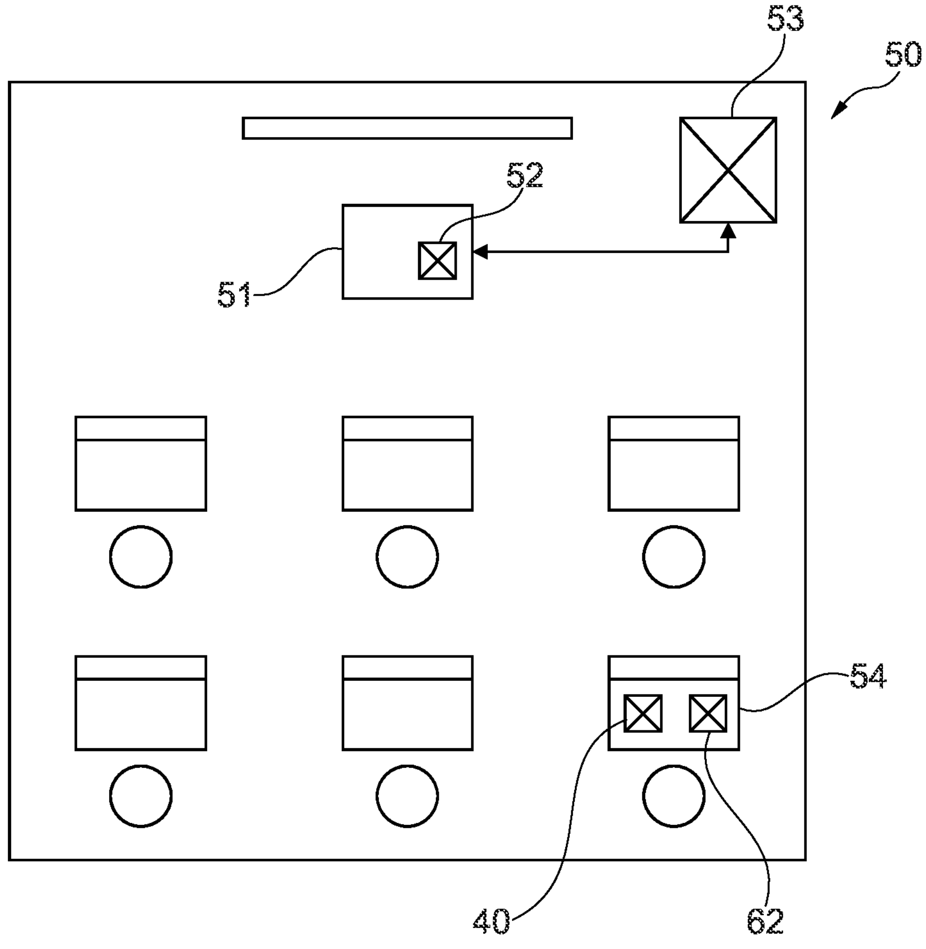
FIG. 11 schematically illustrates a lecture room comprising a system described herein.

FIG. 11 schematically illustrates a lecture room comprising a system described herein.

To further improve user experience and potentially reduce the cost of the system, the audio data 18 of the speech can be obtained by a public address system 53 of a classroom 50. A microphone 52 is placed on a lectern at the front of the classroom 50, near to the presenter. Audio data 18 obtained by the microphone 52 is distributed by the public address system 53 to a loudspeaker system in the room, and the microphone 33 of the writing instrument 40 may pick up the sound of the presenter via the public address system 53. In an example, the writing instrument may receive a digital audio feed comprising the audio data 18 from the public address system 53 via the wireless communication interface 36*c* of the writing instrument 40.

In this example, the pulse signal can also be captured on a further user device 62 and sent to the writing instrument 40. Therefore, the writing instrument 40 can generate the respective vibrational patterns and attention maintenance scores for each user.

In an example, a plurality of writing instruments 40 are assigned to a plurality of students in the classroom 50. Each writing instrument 40 can communicate the assessed attention level to a tablet, smart phone, or personal computer belonging to a teacher. For privacy reasons, measures may be taken to obscure the source of an individual attention measurement, such that the teacher is only presented with an aggregate attention measurement of an entire class. Therefore, a teacher can be presented with information useful to subsequent lesson development.

According to a fourth aspect, there is provided a computer program element comprising machine readable instructions which, when executed by a processor, are configured to cause the processor to perform the computer-implemented method according to the first aspect, or its examples.

According to a fifth aspect, there is provided a computer readable medium comprising the computer program element according to the fourth aspect.

References throughout the preceding specification to "one embodiment", "an embodiment", "one example" or "an example", "one aspect" or "an aspect" means that a particular feature, structure, or characteristic described in connection with the embodiment or example is included in at least one embodiment of the present disclosure. Thus, appearances of the phrases "in one embodiment", "in an embodiment", "one example" or "an example", "one aspect" or "an aspect" in various places throughout this specification are not necessarily all referring to the same embodiment or example.

Furthermore, the particular features, structures, or characteristics can be combined in any suitable combinations and/or sub-combinations in one or more embodiments or examples.

| REFERENCE NUMERALS | |
|---|---|
| P | Proximal end |
| D | Distal end |
| 10 | Method |
| 12 | Obtaining . . . |
| 14 | Generating . . . |
| 16 | Actuating . . . |
| 18 | Audio data |
| 20 | Delimited speech sample |
| 22 | Haptic cue definition |
| 24 | Example of an ECG signal |
| 26 | Example of a PPP signal |

-continued

| REFERENCE NUMERALS | |
|---|---|
| 28 | Example of an ECG signal showing heart rate variability |
| 30 | Apparatus |
| 32 | Power supply |
| 32a | Energy storage |
| 32b | Charging system |
| 33 | Microphone |
| 34 | Haptic feedback generator |
| 34a | Interface electronics |
| 34b | Haptic actuator |
| 35 | Pulse sensor |
| 36 | Controller |
| 36a | Audio processing electronics |
| 36b | Pulse monitoring electronics |
| 36c | Wireless communication interface |
| 36d | Processor |
| 36e | Memory |
| 36f | User interface |
| 38 | Software module |
| 38a | Operating system |
| 38b | Attention monitoring algorithm |
| 38c | Speech to haptic algorithm |
| 39a | Audio pre-processing stage |
| 39b | Word delimiter |
| 39c | Haptic cue generator |
| 39d | Pulse signal pre-processing |
| 39e | Heart rate variability computation |
| 39f | Heart rate variability criterion |
| 40 | Writing instrument |
| 42 | Body |
| 43 | Grip |
| 44 | Clip |
| 45 | Pulse sensing region |
| 46 | Skin contact portion |
| 47 | Nib |
| 50 | Classroom |
| 51 | Lectern |
| 52 | Microphone |
| 53 | Public address system |
| 54 | Desk |
| 60 | System |
| 62 | User device |

The invention claimed is:

1. A computer-implemented method for audio to tactile enhancement comprising:

obtaining audio data comprising a sample of speech, wherein the audio data is processed to normalize amplitude and remove high-frequency noise;

extracting at least one portion of the audio data by pre-processing the audio data, wherein the pre-processing delimits the at least one portion of the audio data from a further portion of the audio data by detecting a transition between a word or syllable in the sample of speech comprised in the audio data;

generating at least one haptic cue definition by performing a first signal processing operation on the at least one portion of the audio data, wherein the first signal processing operation obtains a fundamental frequency of the at least one portion of the audio data, and wherein the at least one haptic cue definition comprises a sampled sine wave having a frequency corresponding to the fundamental frequency of the at least one portion of the audio data, and wherein the at least one haptic cue definition includes a null haptic cue definition for portions of the audio data that do not contain the speech from a presenter; and actuating a haptic actuator comprised in a user device or a writing instrument according to the at least one haptic cue definition, wherein the at least one haptic cue definition is transmitted to the haptic actuator as an actuation signal in near real-time such that a user discernible change in haptic actuation occurs within a latency below a perceptible threshold.

2. The computer-implemented method according to claim 1, further comprising:

obtaining a pulse signal representing a pulse of a user of the user device or the writing instrument, wherein the pulse signal is obtained substantially simultaneously with obtaining the audio data; and applying a second signal processing operation to the pulse signal, wherein the second signal processing operation calculates a heart rate variability signal of the user.

3. The computer-implemented method according to claim 2, further comprising:

monitoring a change of the heart rate variability signal of the user; and when the change of the heart rate variability signal of the user changes, altering the at least one haptic cue definition.

4. The computer-implemented method according to claim 3, wherein if the heart rate variability signal of the user decreases such that it meets a criterion, the at least one haptic cue definition is altered, to thus cause an increase in amplitude of the actuation of the haptic actuator.

5. The computer-implemented method according to claim 1, wherein the user device is a smartwatch or fitness band comprising the haptic actuator.

6. A computer program element comprising machine readable instructions which, when executed by a processor, are configured to cause the processor to perform the computer-implemented method according to claim 1.

7. A computer readable medium comprising the computer program element according to claim 6.

8. A writing instrument for audio to tactile enhancement, comprising:

a processor; and a haptic actuator, wherein the processor is configured to:

obtain audio data comprising a sample of speech, wherein the audio data is processed to normalize amplitude and remove high-frequency noise;

extract at least one portion of the audio data by pre-processing the audio data, wherein the pre-processing delimits the at least one portion of the audio data from a further portion of the audio data by detecting a transition between a word or syllable in the sample of speech comprised in the audio data;

generate at least one haptic cue definition by performing a first signal processing operation on the at least one portion of the audio data, wherein the first signal processing operation obtains a fundamental frequency of the at least one portion of the audio data, and wherein the at least one haptic cue definition comprises a sampled sine wave having a frequency corresponding to the fundamental frequency of the at least one portion of the audio data, and wherein the at least one haptic cue definition includes a null haptic cue definition for portions of the audio data that do not contain the speech from a presenter; and actuate the haptic actuator according to the at least one haptic cue definition, wherein the at least one haptic cue definition is transmitted to the haptic actuator as an actuation signal in near real-time such that a user discernible change in haptic actuation occurs within a latency below a perceptible threshold.

9. The writing instrument according to claim 8, further comprising:

a microphone, wherein the processor is configured to obtain the audio data from the microphone.

10. The writing instrument according to claim 8, further comprising:

a wireless communication interface, wherein the processor is configured to obtain the audio data and/or a pulse signal via the wireless communication interface.

11. The writing instrument according to claim 8, further comprising:

a pulse sensor, wherein the processor is configured to obtain a pulse signal of a user of the writing instrument by measuring a pulse of the user of the writing instrument using the pulse sensor substantially simultaneously with obtaining the audio data, and wherein the processor is configured to apply a second signal processing operation to the pulse signal, and wherein the second signal processing operation calculates heart rate variability of the user.

12. The writing instrument according to claim 11, wherein the processor is further configured to monitor a change of the heart rate variability of the user of the writing instrument, and wherein the processor is configured to alter the at least one haptic cue definition to cause a corresponding increase in amplitude of the actuation of the haptic actuator, when the change of the heart rate variability of the user meets a criterion.

13. The writing instrument according to claim 11, wherein the writing instrument comprises a pulse sensing region.

14. The writing instrument according to claim 13, wherein the writing instrument comprises a body, and wherein the pulse sensing region is disposed on the body, so as to be touched by the user when the writing instrument is in use.

15. The writing instrument according to claim 14, comprising:

a grip, wherein the haptic actuator is disposed within the body and proximate to the grip.

16. A system, comprising:

a writing instrument comprising a haptic actuator configured to be actuated according to at least one haptic cue definition generated from audio data comprising a sample of speech, and a user device comprising a pulse sensor and a wireless communication interface, wherein the user device is configured to:

measure a pulse signal of a user of the user device using the pulse sensor, wherein the pulse signal is obtained substantially simultaneously with obtaining an audio data;

compute a heart rate variability signal of the user based on the pulse signal;

monitoring a change of the heart rate variability signal of the user;

transmit the heart rate variability signal of the user to the writing instrument via the wireless communication interface of the user device, wherein at least one haptic cue definition is altered to increase or decrease an amplitude of actuation of the haptic actuator when an instant value of the heart rate variability signal falls below or rises above a percentage of a moving average of the heart rate variability signal calculated over a time window immediately previous to a present time instant.

17. The system of claim 16, wherein the writing instrument comprises:

a processor configured to obtain the audio data comprising a sample of speech, to generate the at least one haptic cue definition by performing a first signal processing operation on at least one portion of the audio data, and to actuate the haptic actuator according to the at least one haptic cue definition.

18. The system of claim 17, wherein the writing instrument includes a microphone, and wherein the processor is configured to obtain the audio data from the microphone.

* * * * *